United States Patent
Noda et al.

[11] Patent Number: 6,149,588
[45] Date of Patent: Nov. 21, 2000

[54] BLOOD SUGAR VALUE MEASURING METHOD AND APPARATUS

[75] Inventors: Mitsuhiko Noda, Minamiaoyama; Mikio Kimura, Haraichi, both of Japan

[73] Assignees: Mitsui Mining & Smelting Co., Ltd.; Mitsui & Co., Ltd., both of Tokyo, Japan

[21] Appl. No.: 09/314,705

[22] Filed: May 19, 1999

[30] Foreign Application Priority Data

Dec. 25, 1998 [JP] Japan .................................. 10-370120

[51] Int. Cl.[7] .................................................. A61B 5/00
[52] U.S. Cl. .......................................... 600/316; 600/322
[58] Field of Search .................................. 600/310, 316, 600/322

[56] References Cited

U.S. PATENT DOCUMENTS

| | | | |
|---|---|---|---|
| 5,377,674 | 1/1995 | Kuestner | 600/328 |
| 5,499,627 | 3/1996 | Steuer et al. | 600/322 |
| 5,676,143 | 10/1997 | Simonsen et al. | 600/310 |
| 5,792,050 | 8/1998 | Alam et al. | 600/316 |

FOREIGN PATENT DOCUMENTS

5-176917  7/1993  Japan .

*Primary Examiner*—Eric F. Winakur
*Assistant Examiner*—Joseph A. Cadugan
*Attorney, Agent, or Firm*—Pitney, Hardin, Kipp & Szuch LLP

[57] ABSTRACT

Near infrared rays of $\lambda 1$, $\lambda 2$, $\lambda 3$ in wavelength which are different from and near to one another are irradiated from a light source (2) to a part being measured (F) of a living body in such a state that vein bloodstream at the part being measured is stopped by applying a press force of a cuff (8), and the intensities of the transmitted near infrared rays of $\lambda$, $\lambda 2$, $\lambda 3$ in wavelength are detected by a photodetector (4) at the same time. In a processing circuit (14), the absorbance secondary differential value of the near infrared rays by the part being measured (F) is calculated on the basis of the transmitted light intensity detection values thus detected at the same time with respect to the three wavelengths, the variation width thereof within a predetermined time is calculated and then the blood sugar value in the living body is determined from the absorbance secondary differential value variation width on the basis of a calibration curve.

12 Claims, 6 Drawing Sheets

BLOOD SUGAR VALUE MEASURING METHOD AND APPARATUS

BACKGROUND OF THE INVENTION

1. Field of the Invention

The present invention relates to method and apparatus for measuring blood sugar value in a living body under non-invasion condition.

2. Description of the Related Art

In order to set up a standard of the dose of insulin to control the blood sugar value (generally, the concentration value of glucose in blood) of a diabetic, a frequent (for example, several times per day) measurement of blood sugar value is required to be applied to the diabetic. It gives a heavy anguish to a patient to gather blood from the patient every time the measurement is carried out. Therefore, it has been required to measure the blood sugar value of a patient without actually gathering blood from the patient, that is, under non-invasion condition. In order to satisfy this requirement, there is proposed a method of irradiating infrared ray to a part being measured of a patient such as an earlobe, a finger or the like of the patient, detecting the infrared ray transmitted through the part being measured to measure the infrared ray absorption level of the part being measured. According to this method, an absorbance value which relatively accurately reflects the infrared ray absorption by glucose in the part being measured can be obtained by properly selecting the wavelength of the infrared ray being used, and the blood sugar value is determined on the basis of the absorbance value thus obtained.

In the optical blood sugar value measurement under non-invasion condition as described above, the condition of the part being measured (the optical path of infrared ray passing through the part being measured or the like) is varied due to the effect of pulsation or the like, and thus the measurement is unavoidable from accompanying some error due to the above variation. Therefore, it has been strongly required to reduce the measurement error as much as possible.

As a method of reducing the measurement error, it has been indicated that the blood sugar value may be determined, not by measuring the blood sugar value from the absorbance itself, but by using a secondary differential value of the absorbance (Japanese Patent Application Laid-open No. Hei-5-176917). According to this method, the measurement of absorbance is performed by using three wavelengths which are different from one another, but near to one another, and the variation corresponding to the secondary differential calculated through addition and subtraction of the absorbance values thus measured (the secondary differential value of absorbance) is used to determine the blood sugar value.

In the above optical non-invasion blood sugar value measuring method, there is an effect of infrared ray absorption by the components constituting the human body other than blood, and thus it is remarkably preferable to sufficiently remove this effect from the viewpoint of reducing the measurement error.

SUMMARY OF THE INVENTION

An object of the present invention is to provide blood sugar value measuring method and apparatus which can reduce the effect of infrared-ray absorption by components constituting a living body other than blood when the blood sugar value of the living body is determined by using the secondary differential value of absorbance to enhance the measurement precision of a non-invasion blood sugar value measurement.

In order to attain the above object, according to one aspect of the present invention, a blood sugar value measuring method for exposing a part being measured of a living body to near infrared rays having three wavelengths which are different from one another, but near to one another, detecting the intensities of the near infrared rays of the three wavelengths transmitted through the part being measured and then determining the blood sugar value of the living body on the basis of the near infrared rays intensity detection values with respect to the three wavelengths, is characterized by comprising the steps of: calculating the secondary differential value of the absorbance of the near infrared rays of the part being measured from the intensity detection values of the near infrared rays with respect to the three wavelengths; determining the variation width of the secondary differential value of the absorbance as the difference between the maximum and minimum values of the secondary differential value of the absorbance within a predetermined time; and determining the blood sugar value of the living body on the basis of the variation width of the secondary differential value of the absorbance.

In the blood sugar value measuring method of the present invention, the intensities of the transmitted near infrared rays of three wavelengths may be detected at the same time and the secondary differential value of the absorbance may be calculated on the basis of the intensity detection values of the transmitted near infrared rays obtained at the same time.

In the blood sugar value measuring method of the present invention, the variation width of the absorbance value may be calculated as the difference between the maximum and minimum values of the absorbance value within the predetermined time, the variation width of the secondary differential value of the absorbance may be corrected on the basis of the absorbance value variation width to obtain a corrected variation width of the absorbance secondary differential value, and the blood sugar value of the living body may be determined on the basis of the corrected variation width of the absorbance secondary differential variation width.

In the blood sugar value measuring method of the present invention, the correction may be carried out by using the equation: $W'=-V \sin \theta + W \cos \theta$ (here, $\theta$ represents a correction parameter), where $W$ represents the variation width of the absorbance secondary differential value and $W'$ represents the corrected variation width of the absorbance secondary differential value.

In the blood sugar value measuring method of the present invention, the intensities of the near infrared rays of the three wavelengths may be detected while vein bloodstream at the part being measured is stopped by applying a press force to the living body.

In the blood sugar value measuring method of the present invention, the intensities of the near infrared rays of three wavelengths incident to the part being measured may be controlled so that an integration value or an average value for a time of the intensity of at least one of the near infrared rays of three wavelengths transmitted through the part being measured is near to a predetermined value.

In order to attain the above object, according to another aspect of the present invention, a blood sugar value measuring apparatus for exposing a part being measured of a living body to near infrared rays having three wavelengths which are different from one another, but near to one another, detecting the intensities of the near infrared rays of the three wavelengths transmitted through the part being measured and then determining the blood sugar value of the living body on the basis of the near infrared rays intensity detection values with respect to the three wavelengths, is characterized by comprising: a light source for emitting near infrared rays of three wavelengths; a photodetector for detecting the transmitted near infrared rays of three wavelengths transmitted through the living body; and processing means for performing an operation based on the transmitted near infrared rays detection values with respect to the three wavelengths obtained by the photodetector to calculate the secondary differential value of the absorbance of the near infrared rays at the part being measured, calculating the variation width of the absorbance secondary differential value as the difference between the maximum and minimum values of the absorbance secondary differential value within a predetermined time, and determining the blood sugar value of the living body with a calibration curve on the basis of the variation width of the absorbance secondary differential value.

In the blood sugar value measuring apparatus of the present invention, the processing means may calculate the absorbance secondary differential value on the basis of the intensity detection values of the transmitted near infrared rays of three wavelengths which are obtained at the same time by the photodetector.

In the blood sugar value measuring apparatus of the present invention, the processing means may calculate the variation width of the absorbance value as the difference between the maximum and minimum values of the absorbance value within the predetermined time, correct the variation width of the absorbance secondary differential value on the basis of the absorbance value variation width, and then determine the blood sugar value of the living body on the basis of the corrected variation width of the absorbance secondary differential value.

In the blood sugar value measuring apparatus of the present invention, the processing means may perform the correction by using the following equation: W'=−V sine θ+W cos θ(here, θ represents a correction parameter), where W represents the variation width of the absorbance secondary differential value and W' represents the corrected variation width of the absorbance secondary differential value.

The blood sugar value measuring apparatus of the present invention may be further provided with means for applying a press force to the living body.

The blood sugar value measuring apparatus of the present invention may be further provided with means for controlling the intensities of the near infrared rays of three wavelengths incident to the part being measured so that an integration value or an average value for a time of the intensity of at least one of the near infrared rays of three wavelengths transmitted through the part being measured is near to a predetermined value.

According to the blood sugar value measuring method and apparatus of the present invention, the absorbance secondary differential value variation width within a predetermined time is calculated, and the blood sugar value in the living body is determined on the basis of the absorbance secondary differential value variation width. Therefore, the measurement can be performed with sufficiently excluding the effect of the background which contains the effect of the component composition of the body tissue portion, and the measurement precision of the non-invasion blood sugar value measurement can be enhanced. Furthermore, since the blood sugar value is determined on the basis of the absorbance secondary differential value variation width, the measurement result is subject to substantially no influence of the temperature variation. Therefore the present invention does not require the severe condition for the non-invasion blood sugar value measurement.

In addition, the high-precision blood sugar value measurement can be simplified by determining the blood sugar value on the basis of the corrected absorbance secondary differential value variation width.

DETAILED DESCRIPTION OF THE PREFERRED EMBODIMENTS

Preferred embodiments according to the present invention will be described hereunder with reference to the accompanying drawings.

Figure 1:
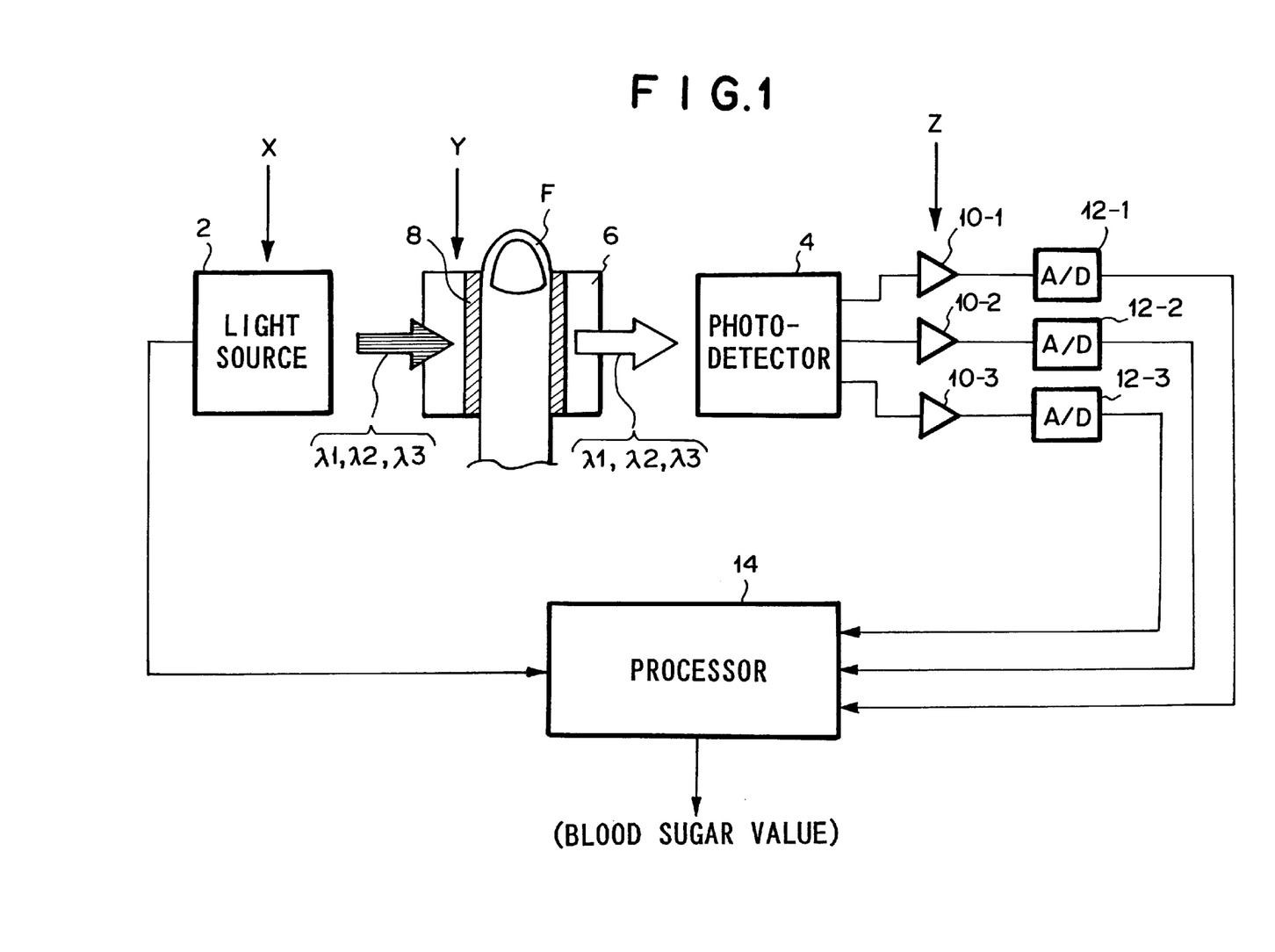
FIG. 1 is a block diagram showing a first embodiment of a blood sugar value measuring apparatus to which a blood sugar value measuring method of the present invention is applied.

FIG. 1 is a block diagram showing the construction of a first embodiment of a blood sugar value measuring apparatus to which a blood sugar value measuring method of the present invention is applied.

In FIG. 1, reference numeral 2 represents a light source, and the light source emits near infrared rays of three wavelengths ($\lambda 1, \lambda 2, \lambda 3$) (which are different from and near to one another ($\lambda 1 < \lambda 2 < \lambda 3$). The wavelengths $\lambda 1, \lambda 2, \lambda 3$ may be set to 902 nm, 912 nm and 922 nm, respectively.

Figure 2A:
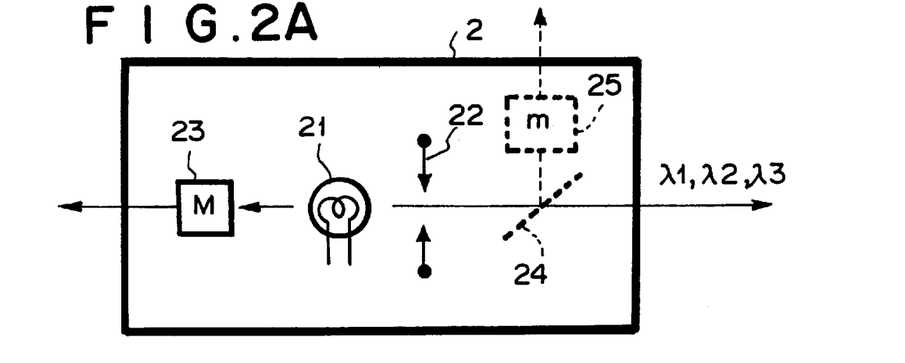
FIGS. 2A and 2B are schematic diagrams showing a light source of the apparatus of FIG. 1.

FIGS. 2A and 2B show specific examples of the light source 2. The light source shown in FIG. 2A has a broad wavelength range light lamp 21 for emitting light containing near infrared rays of the three wavelengths $\lambda 1, \lambda 2, \lambda 3$. A part of the light emitted from the lamp 21 is passed through a diaphragm 22 and forwardly (to the right side in FIG. 2A)

emitted therefrom as light to be irradiated onto a part being measured. The other part of the light emitted from the lamp 21 is incident to a lamp light amount monitor 23 located behind (at the left side in FIG. 2A). In place of the monitor 23, a combination of a half mirror 24 disposed in front of the diaphragm 22 and a monitor 25 for detecting reflected light from the half mirror may be used. A light-amount monitor electrical signal is output from the monitor 23, 25.

Figure 2B:
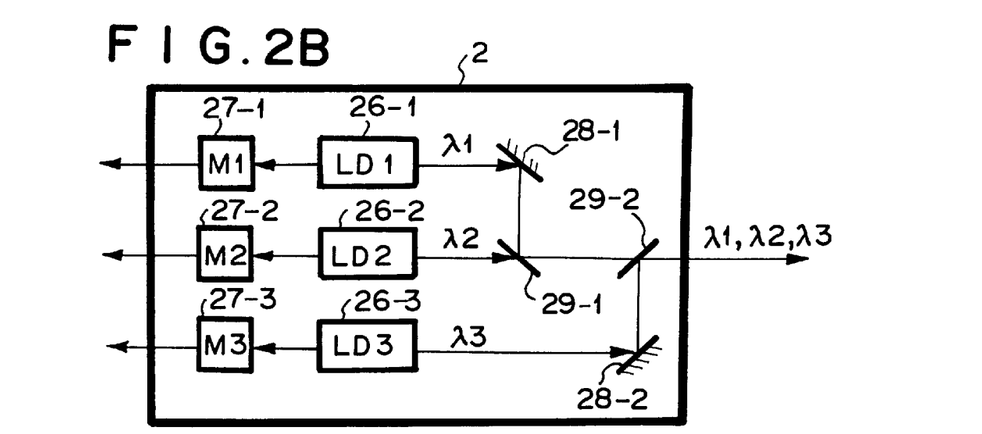

The light source shown in FIG. 2B has semiconductor laser diodes 26-1, 26-2, 26-3 for emitting near infrared rays of wavelengths $\lambda 1$, $\lambda 2$, $\lambda 3$. Light beams to be irradiated to the part being measured are forwardly (to the right side in FIG. 2B) emitted from these lasers. The light beams emitted backwardly (to the left side) from the semiconductor lasers 26-1, 26-2, 26-3 are incident to light-amount monitors 27-1, 27-2, 27-3 respectively, and light-amount monitor electrical signals are output from these monitors. The light beams emitted forwardly from the laser diodes 26-1, 26-3 are combined with the light beam emitted forwardly from the laser diode 26-2 by mirrors 28-1, 28-2 and half mirrors 29-1, 29-2, and then the combined light beams are forwardly emitted as one light flux containing the near infrared rays of the wavelengths $\lambda 1$, $\lambda 2$, $\lambda 3$.

In FIG. 1, reference numeral 4 represents a photodetector, and the photodetector is disposed so as to detect the light beam emitted from the light source 2. A part being measured mount portion 6 in which a part being measured F of a living body such as a human body (for example, a finger or the like) is mounted exists between the photodetector 4 and the light source 2, and a cuff is provided to apply a desired press force to the part being measured F inserted into the part being measured mount portion 6 by air pressure. As the cuff 8 is preferably used one which can keep, for a proper time, such a state that vein bloodstream is stopped (contains sufficient suppression of the vein bloodstream) with keeping artery bloodstream at the part being measured F by adjusting the air injection amount with an air pump. In a travel path of at least near infrared rays of wavelengths $\lambda 1$, $\lambda 2$, $\lambda 3$, the cuff 8 is formed of material or has a structure that allows transmission of the near infrared rays of wavelengths $\lambda 1$, $\lambda 2$, $\lambda 3$ therethrough. For example, a member which covers the part being measured F wholly or a member which is wound around a part nearer to the heart than the part being measured F (if the part being measured F is a finger, the part concerned is a base portion of the finger) may be used as the cuff which can keep the state where the vein bloodstream is stopped while the artery bloodstream is kept at the part being measured F.

Figure 3:
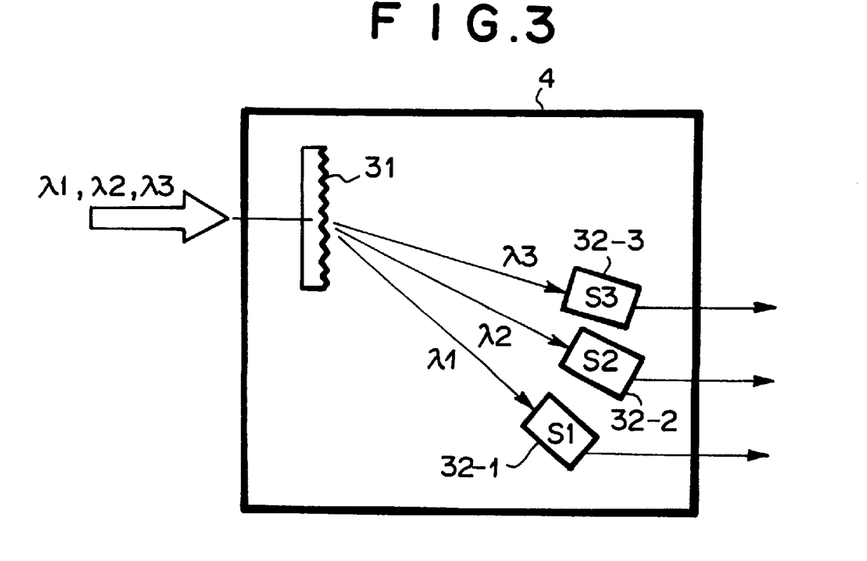
FIG. 3 is a schematic diagram showing a photodetector of the apparatus of FIG. 1.

FIG. 3 shows an embodiment of the photodetector 4. The light containing the near infrared rays of wavelengths $\lambda 1$, $\lambda 2$, $\lambda 3$ which are emitted from the light source 3 and passes through the part being measured F disposed in the part being measured mount portion 6 is split by a diffraction grating 31. The near infrared ray of wavelength $\lambda 1$ is incident to a photodetection unit 32-1, the near infrared ray of wavelength $\lambda 2$ is incident to a photodetection unit 32-2, and the near infrared ray of wavelength $\lambda 3$ is incident to a photodetection unit 32-3. These photodetection units output light-amount detection electrical signals which are proportional to the intensities of the near infrared rays thus detected.

When the light source 2 emits broad wavelength range light as shown in FIG. 2A, a filter for passing therethrough only light having a wavelength which is extremely near to each of the desired wavelengths $\lambda 1$, $\lambda 2$, $\lambda 3$ may be disposed in the photodetector.

The electrical outputs of the three photodetection units 32-1, 32-2, 32-3 of the photodetector 4 (which are proportional to the intensities of the detected light) are amplified by amplifiers 10-1, 10-2, 10-3 whose amplification factors are variable, subjected to A/D conversion by A/D converters 12-1, 12-2, 12-3 and then input to a processing circuit 14 as shown in FIG. 1. The outputs of light-amount monitors 23, 25, 27-1, 27-2, 27-3 of the light source 2 are also subjected to A/D conversion and then input to the processing circuit 14.

The blood sugar value measurement is performed in the processing circuit 14 as follows.

Representing the intensity of light having wavelength $\lambda$ incident to the part being measured F by $Io(\lambda)$ and representing the intensity of light having the wavelengths transmitted through the part being measured F by $I(\lambda)$, the absorbance value $ABS(\lambda)$ of the part being measured F is calculated by $ln(Io(\lambda)/I(\lambda))$. The incident light intensity $Io(\lambda)$ is calculated by multiplying the outputs of the light-source light-amount monitors 27-1, 27-2, 27-3 by predetermined coefficients (in the case of the light-amount monitors 23, 25, multiplied by a predetermined coefficient of every wavelength $\lambda 1$, $\lambda 2$, $\lambda 3$). The absorbance value $ABS(\lambda)$ periodically varies according to pulsation of the part being measured F. That is, the part being measured F contains a body tissue portion and the vein bloodstream and artery bloodstream flowing there, and the optical path of the transmitted light is varied due to pulsation and the component constituent ratio in the path of the transmitted light is also varied. These variations cause the periodical variation of the absorbance $ABS(\lambda)$.

In this embodiment, the absorbance value $ABS(\lambda 1)$, the absorbance value $ABS(\lambda 2)$ and the absorbance value $ABS(\lambda 3)$ are calculated on the basis of $Io(\lambda)$, $I(\lambda)$ which are obtained simultaneously by high-speed sampling every 10 to 20 msec for each of the wavelengths $\lambda 1$, $\lambda 2$, $\lambda 3$, and then the absorbance secondary differential value $ABS''(\lambda 2)$ is calculated on the basis of the absorbance value $ABS(\lambda 1)$, the absorbance value $ABS(\lambda 2)$ and the absorbance value $ABS(\lambda 3)$. The absorbance secondary differential value $ABS''(\lambda 2)$ is obtained with the following equation:

$$ABS''(\lambda 2) = [ABS(\lambda 1) - ABS(\lambda 2)] - [ABS(\lambda 2) - ABS(\lambda 3)]$$

$$= [ABS(\lambda 1) + ABS(\lambda 3)] - 2ABS(\lambda 2)$$

IF $\lambda 2 - \lambda 1 = \lambda 3 - \lambda 2 = \Delta$ and $\lambda 2 = \lambda$, $ABS''(\lambda) = [ABS(\lambda - \Delta) + ABS(\lambda + \Delta)] - 2ABS(\lambda)$ As described above, $\Delta$ can be set to 10 nm or 5 nm.

The light absorption of glucose is varied according to the wavelength of light, and by using this phenomenon three near wavelengths in a wavelength range in which the light absorption variation dependent on the light wavelength appears at maximum are selected. The absorbance secondary differential value is defined as the value corresponding to the wavelength secondary differential of the absorbance for these selected wavelengths.

Figure 4A:
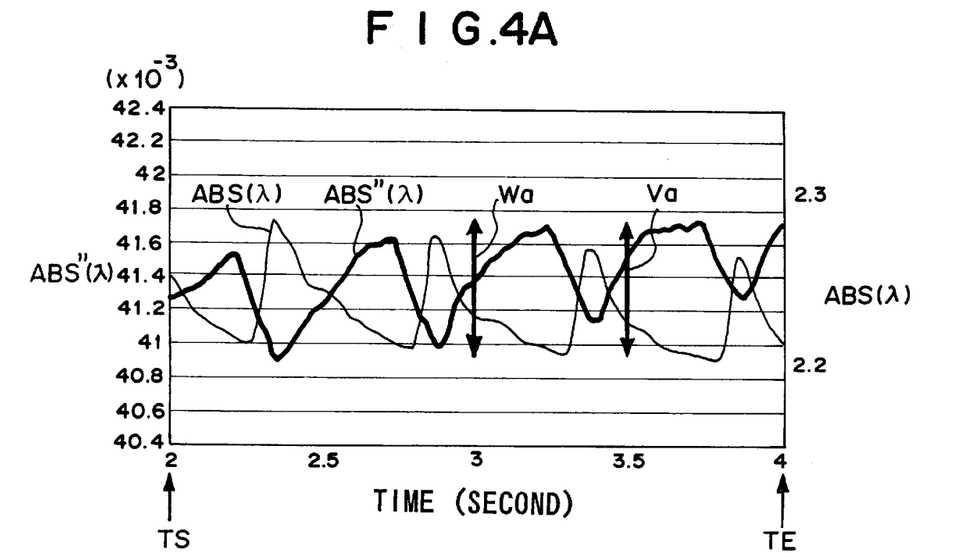
FIGS. 4A and 4B are graphs showing an absorbance value ABS (λ) and an absorbance secondary differential value ABS" (λ) obtained by the apparatus of FIG. 1.
Figure 4B:
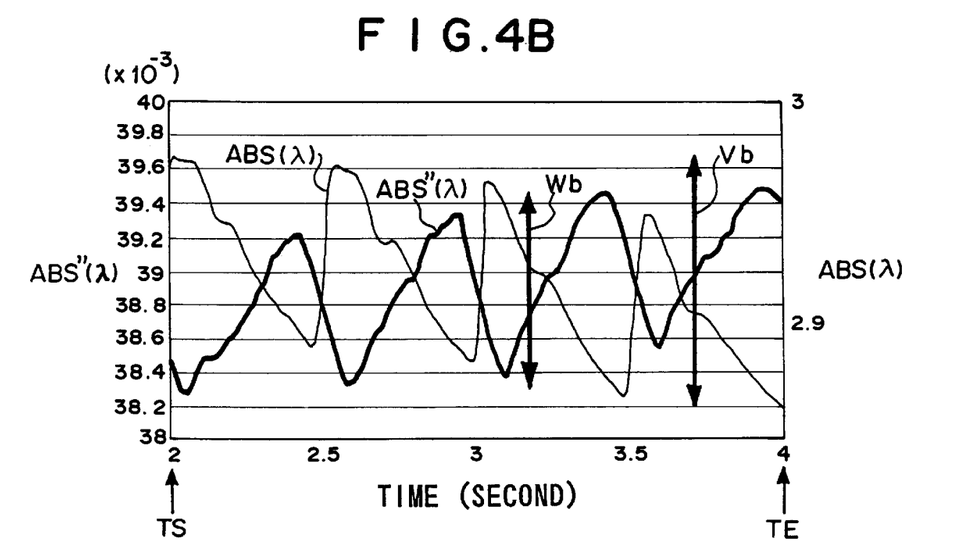

FIGS. 4A and 4B are diagrams showing the time variation of the absorbance value ($\lambda$) and the absorbance secondary differential value $ABS''(\lambda)$. In this case, the injection amount of air into the cuff 8 is adjusted by the air pump by keep such a state that the vein bloodstream at the part being measured F is stopped while the artery bloodstream at the part being measured F is kept. As described above, the absorbance secondary differential value $ABS''(\lambda)$ at each sampling time is obtained by using the absorbance value $ABS(\lambda 1)$, the absorbance ABS(λ2) and the absorbance ABS(λ3) which are obtained at the same time through the high-speed sampling every 10 to 20 msec. The absorbance secondary differential value ABS"(λ) varies with the time variation as shown in FIGS. 4A and 4B. FIGS. 4A and 4B are diagrams for different measurement targets (parts being measured F).

In the processing circuit 14, the variation width W of the absorbance secondary differential value (Wa in FIG. 4A, Wb in FIG. 4B) is determined as the difference between the maximum and minimum values of the absorbance secondary differential value ABS"(λ) within a predetermined time (from time TS until time TE in FIGS. 4A and 4B). The predetermined time may be set to a time period above one period of the pulsation, and it is preferably set to a time period corresponding to several pulsation motions from the viewpoint of the measurement precision. Specifically, the predetermined time may be set to about 2 to 5 seconds, and during this time period, the stop state of only the vein bloodstream can be kept by the cuff.

The absorbance secondary differential value variation width W corresponds to the difference of the absorbance secondary differential values ABS"(λ) when the blood amount in the artery at the part being measured F is maximum and when the blood amount in the artery at the part being measured F is minimum, and the blood amount in the vein and the amount and composition of the components in the body tissue portion at the part being measured F can be regarded as being invariable between the blood-amount maximum state and the blood-amount minimum state in the artery. Accordingly, the absorbance secondary differential value variation width W supports the blood sugar value in blood vessel with sufficiently high precision. The absorbance secondary differential value variation width W is subject to substantially no influence of the temperature.

The absorbance secondary differential value variation width W can be obtained with highest sensitivity by keeping the stop state of only the vein bloodstream with the cuff 8. It has been proved that the difference between the maximum and minimum values of the absorbance value ABS(λ) itself is larger under the state of stopping only the vein bloodstream as compared with the state of stopping both the vein bloodstream and the artery bloodstream (when the press force of the cuff 8 is extremely large) and the state of naturally releasing both the vein bloodstream and the artery bloodstream (when no press force is applied by the cuff 8). Therefore, before the blood sugar value measurement, the cuff press force which maximizes the difference between the maximum value and the minimum value of the absorbance value ABS(λ) itself is tentatively determined while adjusting the press force of the cuff 8, and the cuff press force thus determined is used for the actual measurement of the blood sugar value.

Figure 5:
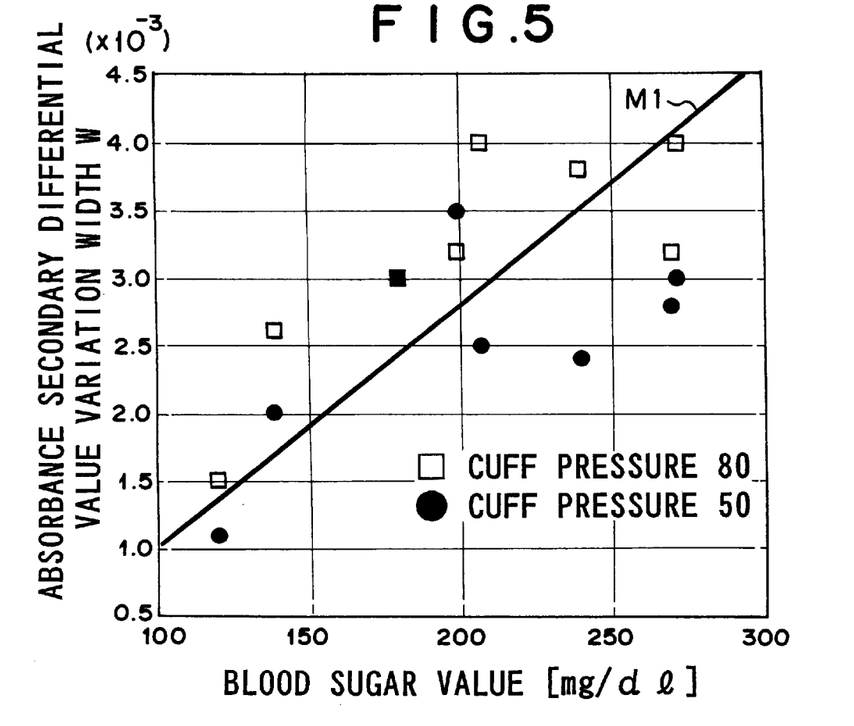
FIG. 5 is a graph showing a calibration curve for the relationship between an absorbance secondary differential value variation width (W) and a blood sugar value used in the apparatus of FIG. 1.

The absorbance secondary differential value variation widths W (Wa, Wb) reflects the blood sugar value of the part being measured F and are different from each other as shown in FIGS. 4A and 4B. The relationship between the absorbance secondary differential value variation width W and the blood sugar value can be determined as a calibration curve in advance by using the method of least square from the actual measurement data obtained in vitro or in vivo. FIG. 5 shows a calibration curve showing the relationship between the absorbance secondary differential value variation width (W) and the blood sugar value. In this case, there is shown a linear calibration curve M1 obtained by linear approximation on the basis of the actual values shown in FIG. 5.

In the processing circuit 14, the blood sugar value corresponding to the absorbance secondary differential value variation width W is selected on the basis of the calibration curve showing the relationship between the absorbance secondary differential value variation width W thus calculated and the blood sugar value for the wavelengths (=λ2) which is beforehand stored. That is, the absorbance secondary differential value variation width W is converted to the blood sugar value.

Figure 6:
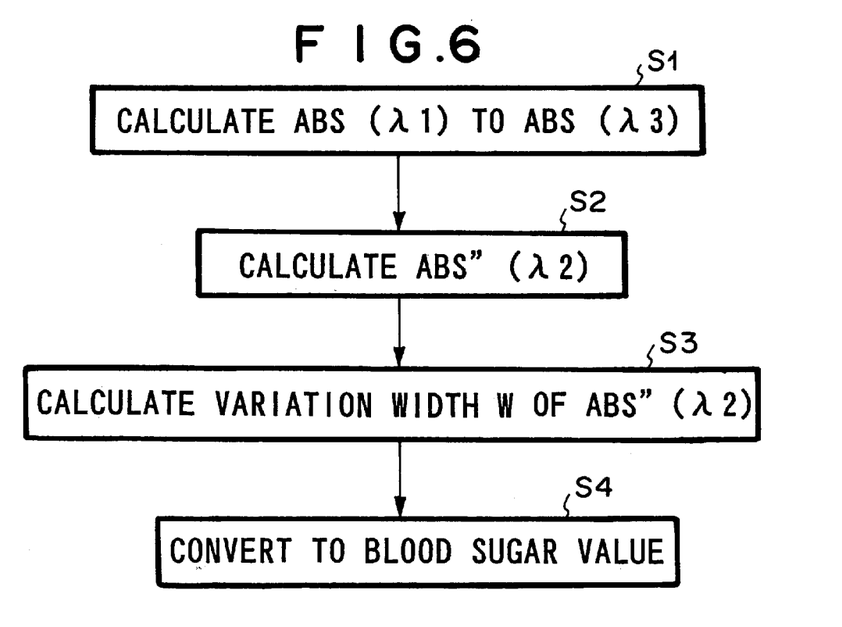
FIG. 6 is a diagram showing a blood sugar value measuring operation of a processing circuit of the apparatus of FIG. 1.

FIG. 6 is a flowchart showing the blood sugar value measuring operation of the processing circuit 14 as described above. That is, in the processing circuit 14, the absorbance values ABS(λ1) to ABS(λ3) are calculated in step S1, the absorbance secondary differential value ABS" (λ2) is calculated in step S2, the variation width W of the absorbance secondary differential value ABS"(λ2) within a predetermined time is calculated in step S3, and then the variation width is converted to the blood sugar value by using the calibration curve in step S4.

The operation of this embodiment is controlled by a controller (not shown). The controller performs not only the control of the operation of the processing circuit, but also the control of the light emission intensity of the lamp 21 of light source 2 or the semiconductor laser diodes 26-1 to 26-3 and the control of the diaphragm 22 of the light source 2 which are performed through a control line X of FIG. 1, the control of cuff pressure which is performed through a control line Y of FIG. 1, and the control of the amplification factor of the amplifiers 10-1, 10-2, 10-3 which is performed through a control line Z of FIG. 1.

Since the dimension of the part being measured F is dependent on each living body, the intensity of light of wavelengths λ1, λ2, λ3 emitted from the light source 2 is controlled through the control line X so that the integration value or time average value for a time of the intensity of at least one transmitted light of λ1, λ2, λ3 detected by the photodetector 4 is near to a predetermined value, thereby keeping the detection condition at the photodetector 4 constant. This control may be initially performed every time the part being measured F is varied.

The transmitted light of λ1, λ2, λ3 in wavelength is detected while the cuff pressure of the cuff 8 is controlled through the control line Y so that it is applied to the pulsating part being measured F, whereby the state of stopping only the vein bloodstream can be kept and the absorbance secondary ifferential value variation width W can be detected with high ensitivity in addition to the effect of keeping the detection ondition at the part being measured constant.

The amplification factor of each of the amplifiers 10-1, 10-2, 10-3 is controlled through the control line Z to set the processing condition of the processing system to a desired one.

Next, a second embodiment of the blood sugar value measuring apparatus according to the present invention to which the blood sugar value measuring method of the present invention is applied.

Like the first embodiment, the second embodiment has the same apparatus construction as shown in FIGS. 1 to 3, and the time variation of the absorbance value ABS(λ) and the absorbance secondary differential value ABS"(λ) is obtained.

This embodiment is different from the first embodiment in the processing of the processing circuit 14. That is, the absorbance value variation width V [Va in FIG. 4A, Vb in FIG. 4B] is calculated as the difference between the maximum and minimum values of the absorbance value ABS(λ) within the predetermined time (from the time TS until the time TE in FIGS. 4A and 4B). The absorbance secondary differential value variation width W is corrected on the basis of the absorbance value variation width V to obtain the corrected absorbance secondary differential value variation width W', and the blood sugar value in the living body is determined on the basis of the corrected absorbance secondary differential value variation width W'. This correction may be performed by using the following equation:

$$W' = -V \sin \theta + W \cos \theta \quad (1)$$

(here, θ represents a correction parameter)

Figure 7:
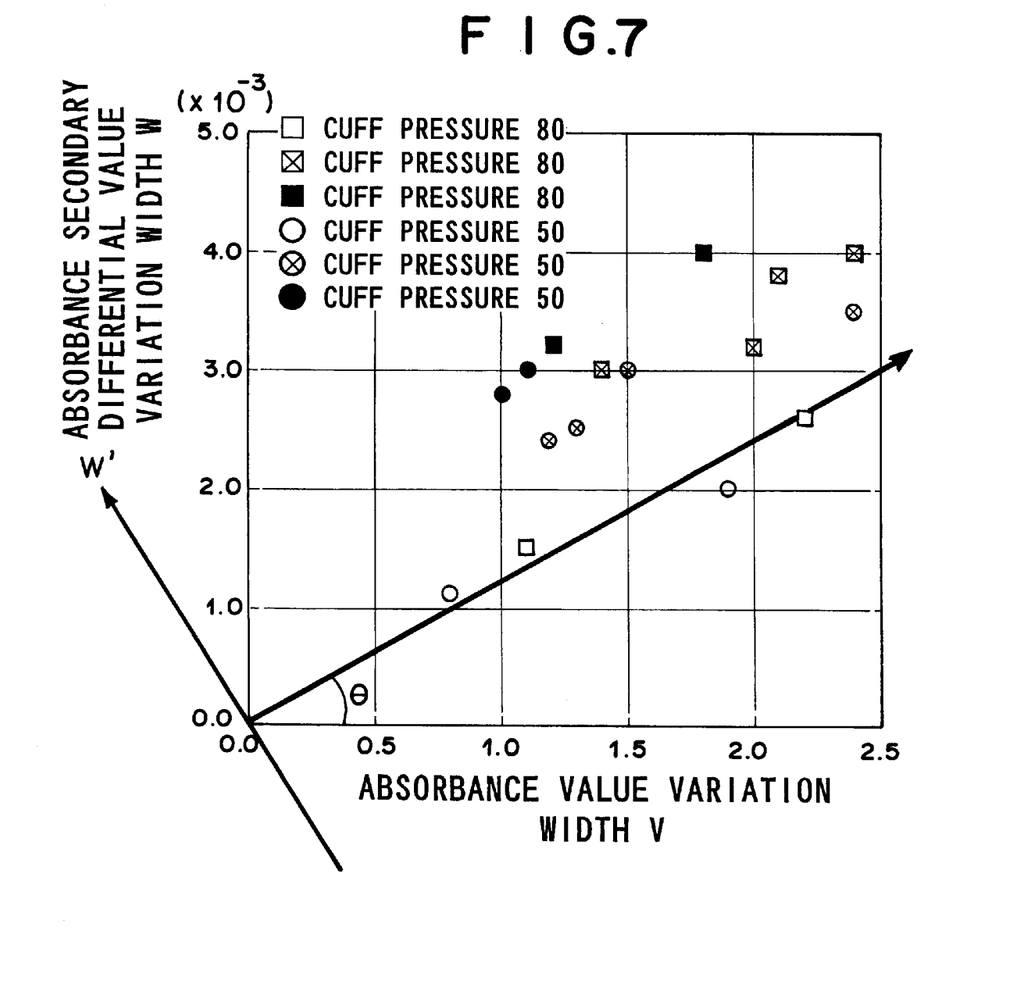
FIG. 7 is a diagram showing the relationship between the absorbance value variation width V and the absorbance secondary differential value variation width W.

The significance of the correction will be described. The inventors of this invention have found out that the absorbance secondary differential value variation width W has a correlation with the absorbance value variation width V. That is, as is apparent from the actual measurement values shown in FIG. 7, the absorbance secondary differential value variation width W increases as the absorbance value variation width V increases. Therefore, if the corrected absorbance secondary differential value variation width W' is obtained as shown in the equation (1) by using a new coordinate system obtained by rotating the coordinate axis by an angle of θ as shown in FIG. 7, the variation of the corrected absorbance secondary differential value variation width W' thus obtained is smaller than the absorbance secondary differential value variation width W before the correction. The value of θ may be set on the basis of the actual measurement values obtained by an experiment in advance.

Figure 8:
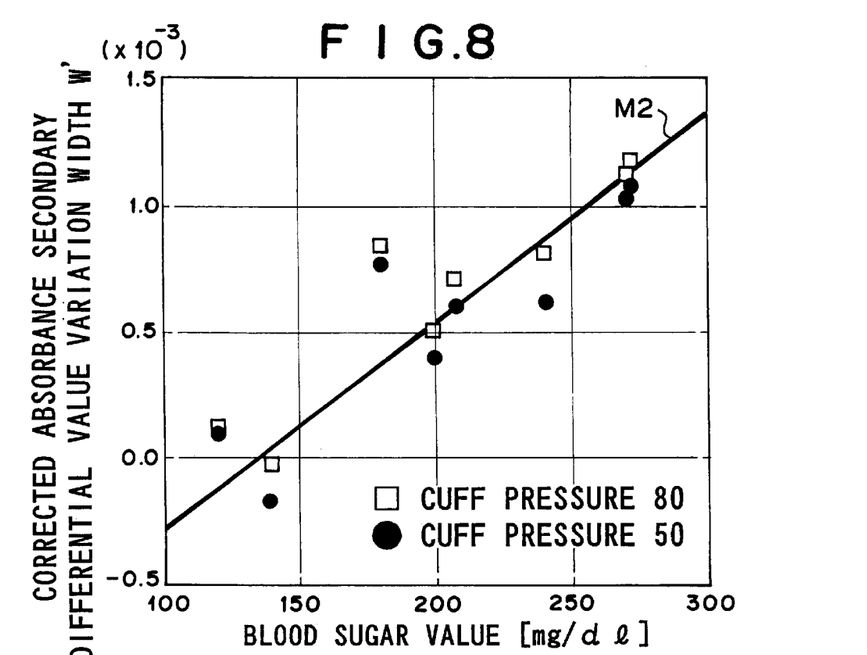
FIG. 8 is a graph showing a calibration curve for the relationship between a corrected absorbance secondary differential value variation width (W') and a blood sugar value in a second embodiment of the blood sugar value measuring apparatus to which the blood sugar value measuring method of the present invention is applied.

FIG. 8 shows a calibration curve showing the relationship between the corrected absorbance secondary differential value variation width (W') and the blood sugar value. In this case, FIG. 8 shows a linear calibration curve M2 obtained by linear approximation based on the actual measurement values shown in FIG. 8.

In the processing circuit 14, the blood sugar value corresponding to the corrected absorbance secondary differential value variation width W' is selected on the basis of the calibration curve showing the relationship between the corrected absorbance secondary differential value variation width W' thus calculated and the blood sugar value for the wavelength λ(=λ2) which is beforehand stored. That is, the corrected absorbance secondary differential value variation width W' is converted to the blood sugar value.

Figure 9:
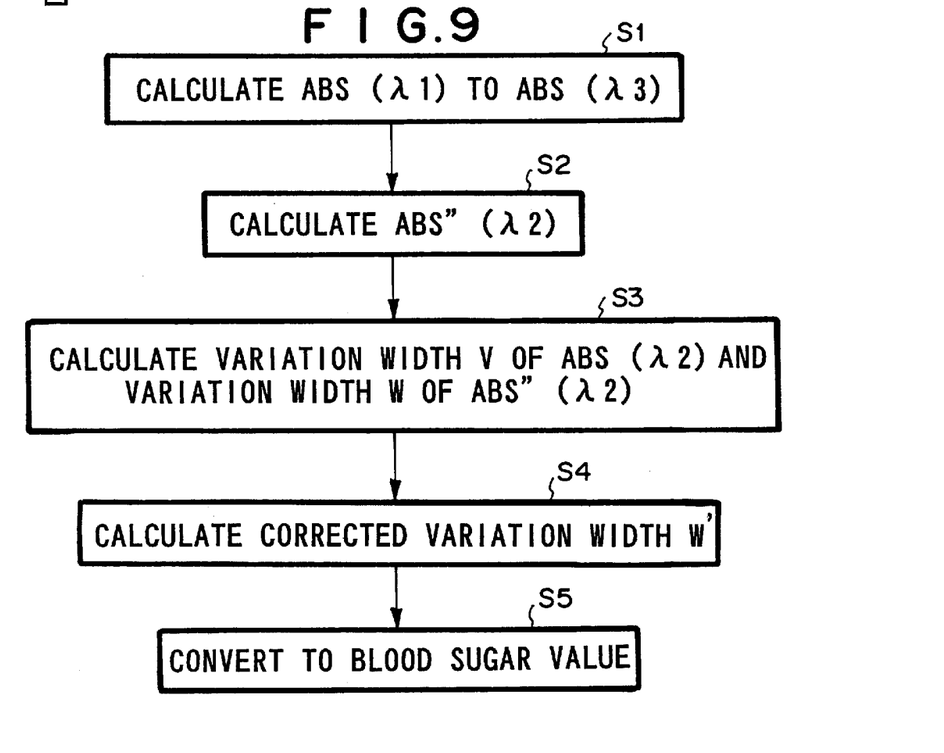
FIG. 9 is a diagram showing the blood sugar value measuring operation of a processing circuit of the second embodiment of the blood sugar value measuring apparatus of the present invention to which the blood sugar value measuring method of the present invention is applied.

FIG. 9 is a flowchart showing the above blood sugar value measuring operation of the processing circuit 14. That is, in the processing circuit 14, the absorbance values ABS(λ1) to ABS(λ3) are calculated in step S1, the absorbance secondary differential value ABS"(λ2) is calculated in step S2, the variation widths V, W of the absorbance value ABS(λ2) and the absorbance secondary differential value ABS"(λ2) within a predetermined time are calculated in step S3, the corrected absorbance secondary differential value variation width W' is calculated by using the equation (1) in step S4, and then the corrected variation width W' is converted to the blood sugar value by using the calibration curve in step S5.

According to this embodiment using the corrected absorbance secondary differential value variation width W' as described above, there is obtained an effect of reducing the dispersion of the blood value measurement due to the difference (variation) in measurement condition (the difference of the part being measured which contains the difference of the measurement target (body being examined), the difference of the cuff pressure of the measuring apparatus, the difference of the amplification factor of the amplifier of the apparatus, the difference of the irradiation light intensity, etc.) Therefore, it is not necessarily required to keep the measurement condition constant to enhance the measurement precision, and thus the blood sugar value measurement can be more easily performed with high precision.

What is claimed is:

1. A blood sugar value measuring method comprising the steps of exposing a part being measured of a living body to near infrared rays having three wavelengths which are different from one another, but near to one another: detecting the intensities of the near infrared rays of the three wavelengths transmitted through the part being measured:

calculating the secondary differential value of the absorbance of the near infrared rays of the part being measured from the intensity detection values of the near infrared rays with respect to the three wavelengths;

determining the variation width of the secondary differential value of the absorbance as the difference between the maximum and minimum values of the secondary differential value of the absorbance within a predetermined time; and determining the blood sugar value of the living body on the basis of the variation width of the secondary differential value of the absorbance.

2. The blood sugar value measuring method as claimed in claim 1, wherein the intensities of the transmitted near infrared rays of three wavelengths are detected at the same time and the secondary differential value of the absorbance is calculated on the basis of the intensity detection values of the transmitted near infrared rays obtained at the same time.

3. The blood sugar value measuring method as claimed in claim 1, wherein the variation width of the absorbance value is calculated as the difference between the maximum and minimum values of the absorbance value within the predetermined time, the variation width of the secondary differential value of the absorbance being corrected on the basis of the absorbance value variation width to obtain a corrected variation width of the absorbance secondary differential value, and the blood sugar value of the living body being determined on the basis of the corrected variation width of the absorbance secondary differential variation width.

4. The blood sugar value measuring method as claimed in claim 3, wherein the correction is carried out by using the equation: W'=−V sin θ+W cos θ where θ, represents a correction parameter, W represents the variation width of the absorbance secondary differential value and W' represents the corrected variation width of the absorbance secondary differential value.

5. The blood sugar value measuring method as claimed in claim 1, wherein the intensities of the near infrared rays of the three wavelengths are detected while venous bloodflow at the part being measured is stopped by applying a press force to the living body.

6. The blood sugar value measuring method as claimed in claim 1, wherein the intensities of the near infrared rays of three wavelengths incident to the part being measured are controlled so that an integration value or an average value for a time of the intensity of at least one of the near infrared rays of three wavelengths transmitted through the part being measured is near to a predetermined value.

7. A blood sugar value measuring apparatus for exposing a part being measured of a living body to near infrared rays having three wavelengths which are different from one another, but near to one another, detecting the intensities of the near infrared rays of the three wavelengths transmitted through the part being measured and then determining the blood sugar value of the living body on the basis of the near infrared rays intensity detection values with respect to the three wavelengths, comprising:

a light source for emitting near infrared rays of three wavelengths;

a photodetector for detecting the transmitted near infrared rays of three wavelengths transmitted through the living body; and processing means for performing processing based on the transmitted near infrared rays detection values with respect to the three wavelengths obtained by said photodetector to calculate the secondary differential value of the absorbance of the near infrared rays at the part being measured, determining the variation width of the absorbance secondary differential value as the difference between the maximum and minimum values of the absorbance secondary differential value within a predetermined time, and determining the blood sugar value of the living body by using a calibration curve based on the variation width of the absorbance secondary differential value.

8. The blood sugar value measuring apparatus as claimed in claim 7, wherein said processing means calculates the absorbance secondary differential value on the basis of the intensity detection values of the transmitted near infrared rays of three wavelengths which are obtained at the same time by said photodetector.

9. The blood sugar value measuring apparatus as claimed in claim 7, wherein said processing means calculates the variation width of the absorbance value as the difference between the maximum and minimum values of the absorbance value within the predetermined time, corrects the variation width of the absorbance secondary differential value on the basis of the absorbance value variation width, and then determines the blood sugar value of the living body on the basis of the corrected variation width of the absorbance secondary differential value.

10. The blood sugar value measuring apparatus as claimed in claim 9, wherein said processing means performs the correction by using the following equation: $W' = -V \sin \theta + W \cos \theta$ where $\theta$, represents a correction parameter, $W$ represents the variation width of the absorbance secondary differential value, and $W'$ represents the corrected variation width of the absorbance secondary differential value.

11. The blood sugar value measuring apparatus as claimed in claim 7, further comprising means for applying a press force to the living body.

12. The blood sugar value measuring apparatus as claimed in claim 7, further comprising means for controlling the intensities of the near infrared rays of three wavelengths incident to the part being measured so that an integration value or an average value for a time of the intensity of at least one of the near infrared rays of three wavelengths transmitted through the part being measured is near to a predetermined value.

* * * * *